United States Patent [19]

Latella et al.

[11] Patent Number: 4,980,087
[45] Date of Patent: Dec. 25, 1990

[54] ETHER SULFATES OF A MIXTURE OF BRANCHED 1-DECANOLS

[75] Inventors: Anthony Latella, Flanders, N.J.; Robert V. Casciani, Matthews, N.C.

[73] Assignee: Sandoz Ltd., Basel, Switzerland

[21] Appl. No.: 409,837

[22] Filed: Sep. 20, 1989

Related U.S. Application Data

[60] Division of Ser. No. 226,266, Jul. 29, 1988, Pat. No. 4,879,399, which is a continuation of Ser. No. 74,633, Jul. 17, 1987, abandoned, which is a continuation of Ser. No. 819,181, Jan. 15, 1986, abandoned.

[51] Int. Cl.⁵ ............................................... C11D 1/12
[52] U.S. Cl. ..................................... 252/545; 252/551
[58] Field of Search ................... 252/551, 545; 558/34, 558/27

[56] References Cited

U.S. PATENT DOCUMENTS

| | | |
|---|---|---|
| 2,174,761 | 10/1939 | Schuette et al. . |
| 2,677,700 | 5/1954 | Jackson et al. . |
| 3,270,038 | 8/1966 | Marshall et al. . |
| 3,843,706 | 10/1974 | Weil et al. . |
| 3,931,271 | 1/1976 | Baumann et al. . |
| 3,959,186 | 5/1976 | Harris . |
| 4,051,047 | 9/1977 | Liston . |
| 4,293,428 | 10/1981 | Gale et al. . |
| 4,299,994 | 11/1981 | Stahel . |
| 4,608,197 | 8/1986 | Kesling, Jr. et al. . |
| 4,879,399 | 11/1989 | Latella et al. . |

FOREIGN PATENT DOCUMENTS

1445997  8/1976  United Kingdom .

OTHER PUBLICATIONS

Sagarin, Cosmetics, Science and Technology, pp. 396 and 402 (1957).

*Primary Examiner*—Alan Siegel
*Attorney, Agent, or Firm*—Gerald D. Sharkin; Richard E. Vila; Joseph J. Borovian

[57] ABSTRACT

The invention relates to novel ether sulfates based on a mixture of branched 1-decanols and to their use as surface active agents. The novel ether sulfates are especially useful as the essential surfactant component in shampoo compositions, which compositions exhibit good foaming properties with little or no irritation potential.

11 Claims, No Drawings

ETHER SULFATES OF A MIXTURE OF BRANCHED 1-DECANOLS

This is a division of application Ser. No. 07/266,266, filed July 29, 1988, now issued as U.S. Pat. No. 4,879,399, which in turn is a continuation of application Ser. No. 07/074,633, filed July 17, 1987, now abandoned, which in turn is a continuation of application Ser. No. 06/819,181, filed Jan. 15, 1986, now abandoned.

This invention relates to a new class of surface active agents. More particularly, it relates to novel ether sulfates based on a mixture of branched 1-decanols and to their use as surface active agents and, more especially, to their use as surfactants in shampoo compositions.

To an outsider looking in, the search for a surfactant for use in shampoo compositions is relatively easy since new surfactants appear in the literature regularly. However, and as is well known by those skilled in the art, the formulation of shampoo compositions for human hair is a highly specialized field involving many considerations, viz., cleaning ability, foaming action, mildness, etc. More often than not, a surfactant is chosen primarily on the basis of its cleaning ability at the expense of serious compromises in overall product behavior.

In the past, soap-based shampoo compositions were employed. Unfortunately, they suffered from the disadvantage of dulling the hair due to the precipitation thereon of lime and magnesium soap or the like, especially in hard water. In addition, such precipitates considerably reduced the foaming action of the shampoo compositions. Faced with the problems exhibited by soap-based shampoo compositions, those skilled in the art attempted to overcome these drawbacks by the substitution, in part, of synthetic organic detergents, e.g., sulfates and sulfonates, for the soap. However, shampoo compositions based on mixtures of synthetic detergents and soaps appear to be rather deficient and offer little in value to the demanding consumer. For instance, when such mixtures are brought into contact with calcium ions in the water, the lime soaps which necessarily form must be dispersed by the synthetic detergent. Consequently, not only is a part of the soap lost by binding to calcium, when such ions are present, but also part of the synthetic detergent is consumed as a dispersing agent for the lime soap formed and thereby loses a certain degree of its cleaning action. In this connection, it should be kept in mind that in the washing of human hair, even a professional hairdresser normally uses tap water.

More recently, shampoo compositions have surfaced which contain, as the essential cleaning component, a synthetic detergent or a mixture thereof, exclusively. However, although such shampoo compositions exhibit acceptable cleaning and foaming properties, the presence of the synthetic detergent or mixture thereof appears to enhance the irritation potential of the shampoo compositions, thereby making them unacceptable from a mildness standpoint. In an effort to overcome the enhanced irritation potential of synthetic detergent-based shampoo compositions, the skilled artisan has modified the synthetic detergent component, e.g., a higher alkyl ether sulfate of the formula $$R(OCH_2CH_2)_m\text{-}OSO_3M$$

where R is $C_{10}$–$C_{15}$alkyl, m is an integer 1 to 3 and M is a cation, by increasing the level of ethylene oxide. However, such a modification, although somewhat ameliorating the irritation potential of the above-identified alkyl ether sulfates, adversely affects the foaming properties of the shampoo compositions.

Accordingly, it is an object of the present invention to provide a new class of surface active agents. It is another object of the present invention to provide a new class of surface active agents which may be employed as the essential surfactant in shampoo compositions. It is still another object of the present invention to provide a new class of ether sulfates which may be employed as the essential surfactant in shampoo compositions, wherein said compositions exhibit exceptional cleaning and foaming properties. It is yet still another object of the present invention to provide a new class of ether sulfates which may be employed as the essential surfactant in shampoo compositions, wherein said compositions not only exhibit exceptional cleaning and foaming properties but little or no irritation potential as well.

The attainment of the above objects is made possible by a mixture of ether sulfates of formula I:

$$R(OC_3H_6)_m(OC_2H_4)_nOSO_3M \qquad \text{I}$$

wherein

R is the residue of a mixture of primary, aliphatic alcohols, at least 70 mol % of which is branched 1-decanols, the remaining components consisting essentially of primary, aliphatic alcohols having an average of 8 to 12 carbon atoms;

m is an integer 2 to 13;

n is an integer 6 to 15; and

M is a cation.

R is preferably the residue of a mixture of primary, aliphatic alcohols, at least 90 mol % of which is branched 1-decanols. More preferably, R is the residue of a mixture of primary, aliphatic alcohols, at least 95 mol % of which is branched 1-decanols. Even more preferably, R is the residue of a mixture of primary, aliphatic alcohols, at least 95 mol % of which is branched 1-decanols and the major isomers are trimethyl-1-heptanols.

The variable, m, is preferably 3 to 12, more preferably 3 to 10, and most preferably 3 to 9.

The variable, n, is preferably 6 to 13, more preferably 6 to 12, and most preferably 8 to 12.

M is preferably a cation selected from alkali metal, alkaline earth metal, ammonium, mono-, di- and tri-$C_2$–$C_4$alkanolammonium, mono-, di-, tri- and tetra-$C_1$–$C_4$alkylammonium pyridinium and morpholinium. More preferably, M is a cation selected from sodium, potassium, ammonium, mono-, di- and tri-$C_2$–$C_4$alkanolammonium and mono-, di-, tri- and tetra-$C_1$–$C_4$alkanolammoinum. Even more preferably, M is a cation selected from sodium, potassium, ammonium, mono-, di- and tri-$C_2$–$C_4$alkanolammonium, Preferred mixtures of compounds are those of formula Ia:

$$R'(OC_3H_6)_{m'}(OC_2H_4)_{n'}\text{-}OSO_3M' \qquad \text{Ia}$$

wherein

R' is the residue of a mixture of primary, aliphatic alcohols, at least 90 mol % of which is branched 1-decanols;

m' is an integer 3 to 12;

n' is an integer 6 to 13; and

M' is a cation selected from alkali metal, alkaline earth metal, ammonium, mono-, di- and tri-$C_2$-$C_4$alkanolammonium and mono-, di-, tri- and tetra-$C_1$-$C_4$ alkylammonium.

The more preferred mixtures of compounds are those of formula Ib:

   Ib wherein
R" is the residue of a mixture of primary, aliphatic alcohols, at least 95 mol % of which is branched 1-decanols;
m" is an integer 3 to 10;
n" is an integer 6 to 12; and
M" is a cation selected from sodium, potassium, ammonium, mono-, di- and tri-$C_2$-$C_4$alkanolammonium and mono-, di-, tri- and tetra-$C_1$-$C_4$alkylammonium.

The most preferred mixtures of compounds are those of formula Ic:

   Ic wherein
R''' is the residue of a mixture of primary, aliphatic alcohols, at least 95 mol % of which is branched 1-decanols and the major isomers are trimethyl-1-heptanols;
m''' is an integer 3 to 9;
n''' is an integer 8 to 12; and
M''' is a cation selected from sodium, potassium, ammonium and mono-, di- and tri-$C_2$-$C_4$alkanolammonium.

The compounds of formula I are produced by more or less conventional methods. Thus, the novel ether sulfates of this invention may be prepared by sulfating the adduct resulting from the propoxylation and ethoxylation of a specific mixture of primary, aliphatic alcohols as defined above with a conventional sulfating agent in a manner conventional for the sulfation of similar primary alcohols.

More particularly, a catalytic amount, e.g., from about 0.2% to 1%, preferably 0.3% to 0.75%, by weight of the total amount of reactants, including the respective alkylene oxides, of an alkaline catalyst is added to the alcohol mixture to be alkoxylated.

Catalysts which may be employed include alkali metal hydroxides, alkali metal and alkaline earth metal oxides, alkali metal acetates and dimethylamine, and mixtures thereof. Preferred catalysts are the alkali metal hydroxides and the alkaline earth metal oxides. Other types of catalysts commonly used for alkylene oxide condensation reactions may also be employed.

Optionally, a small amount of a reducing agent may be added to the alcohol mixture to be alkoxylated to minimize discoloration of the resulting polyalkoxylated alcohol mixture. Suitable reducing agents which may be employed include sodium borohydride, lithium aluminum hydride, diborane and the like, preferably sodium borohydride.

An amount of propylene oxide calculated to provide the desired degree of propoxylation is then introduced and the resulting mixture is allowed to react until the propylene oxide is consumed, as indicated by a drop in reaction pressure. A similar introduction and reaction of a calculated amount of ethylene oxide serves to provide the second block which completes the alkoxylation. Customarily, the alkoxylated product is finally treated with weak acid, e.g., glacial acetic acid, to neutralize any basic catalyst residues.

It should be understood that each separate alkoxylation procedure serves to introduce a desired average number of alkylene oxide units per alcohol molecule. Thus, for example, the initial treatment of an alcohol mixture with m moles of propylene oxide per mole of alcohol serves to effect the propoxylation of each alcohol moiety with propylene oxide to an average of m propylene oxide moieties per alcohol moiety, although some alcohol moieties will have become combined with more than m propylene oxide moieties and some will have become combined with less than m. The variation in the number of alkylene oxide moieties is not critical as long as the average for the number of units in each block is within the limits set out for the m and n terms in formula I above, which terms, as average values, are other than whole numbers in some instances.

Each alkoxylation is conducted at an elevated temperature and pressure. Suitable reaction temperatures are from about 120° C. to about 220° C., preferably, 130° C. to 180° C. and, more preferably, 140° C. to 160° C. A suitable reaction pressure is achieved by introducing to the reaction vessel the required amount of propylene oxide or ethylene oxide, each of which has a high vapor pressure at the desired reaction temperature. The pressure serves as a measure of the degree of reaction and each alkoxylation is considered to be complete when the pressure no longer decreases with time.

For best results, it is desirable to carry out the alkoxylation under relatively moisture-free conditions and to avoid side reactions which form water. To dry the reaction vessel and connections, they may be swept out with dry, oxygen-free gas, e.g., nitrogen, before introducing the charge. The catalyst or catalyst mixture should also be dry, or substantially so. The propylene oxide and ethylene oxide should preferably be purified to remove moisture and any impurities which are capable of entering into side reactions which yield water.

The resulting alkyl, polyalkoxide intermediates are then sulfated employing a conventional sulfating agent such as sulfuric acid, sulfamic acid, sulfur trioxide and chlorosulfonic acid, and utilizing either a batch or continuous process. For purposes of this invention, it has been found suitable to employ chlorosulfonic acid in a batch process.

Typically, the alkyl, polyalkoxide intermediate is introduced into a reaction vessel, purged with nitrogen and heated under vacuum to remove trace water. With stirring, a 10% to 20% molar excess of chlorosulfonic acid is then added, dropwise, and the reaction temperature is maintained between 30° and 35° C. until addition is complete. After allowing the reaction to proceed for 1½ to 2 hours, the resultant mixture is then poured onto cracked ice and the pH adjusted to between 6.5 to 7.5 with sodium hydroxide.

The most conspicuous property of the compounds of formula I is their great activity at surfaces and interfaces, making them especially useful as surface active agents. The uses to which surface active agents can be put are numerous and well known and, as a result, the possible applications of these new compounds are extremely varied. Thus, the surface active agents of the present invention are suitable as emulsifiers, dispersing agents, detergents, wetting agents, levelling agents and the like in the textile, leather, paper, lacquer, personal care, e.g., toiletries, cosmetics, etc., and rubber industries. For instance, they can be used as wetting agents or detergents in the treating and refining of textiles; and for converting liquid or solid substances which per se are insoluble in water (such as hydrocarbons, higher alcohols, oils, fats, waxes and resins) into creamy emulsions, clear solutions or fine, stable dispersions.

In addition, the compounds of formula I are valuable emulsifiers for insecticide compositions and agricultural sprays such as DDT, 2,4-D and the like; are valuable for use as additives to petroleum products, hydraulic fluids, lubricating oils, cutting oils and greases; may be employed as coating aids for use in coating compositions comprising a hydrophilic, film-forming colloid; may be employed as tackifiers in the adhesive layer of adhesive tapes in, e.g., the photographic industry; and as foaming agents and emulsifying agents in a wide variety of food products.

The ether sulfates of the instant invention are especially useful as the essential surfactant component in shampoo compositions. Their incorporation serves to enhance not only the detergency and foaming properties of the shampoo compositions but the tactile properties as well. Such shampoo compositions will normally contain from about 5% to about 50% of an ether sulfate of formula I, preferably from about 5% to about 40%, and more preferably from about 10% to about 30%. As indicated above, the ether sulfates may be employed as the sole surfactant thereof, i.e., totally replace the conventional surfactants such as the alkyl-EO sulfates, which is the more preferred feature of the instant invention, or the ether sulfates may be employed in combination with conventional surfactants, i.e, partially replace the latter.

The shampoo compositions can contain other ingredients commonly found in such type compositions. For example, a fatty alkanolamide, or a mixture thereof, may be employed to assist in foam stabilization, foam boosting and in providing a cosmetically acceptable viscosity. In general, a $C_8$–$C_{18}$ mono- or dialkanolamide of the 1:1 variety (prepared by reacting equimolar amounts of the methyl ester of an appropriate carboxylic acid and mono- or dialkanolamine) is employed. A suitable example of a monoalkanolamide is cocomonoethanolamide, and typical examples of suitable dialkanolamides are lauric diethanolamide and cocodiethanolamide.

Conditioners may also be employed and such may be quaternary ammonium compounds such as dimethyl distearyl ammonium chloride and cationic polymers such as Cartaretin F-23 (Sandoz Corporation) and Polymer JR (Union Carbide). These materials are utilized to improve the combability and manageability of damaged hair and to reduce static build-up on dry hair.

In order to improve the sheen of the hair, an oil may be present in the shampoo compositions. Such may be a silicone oil such as dimethylpolysiloxane or other conventional polysiloxanes, olive oil, or a light mineral oil.

The amount of water or aqueous vehicle to be included depends upon the desired consistency of the final product. It is possible to vary the amount of water present to formulate, for example, a thick-flowing liquid, lotion or gel. Inorganic salts such as sodium chloride can also be employed to control the viscosity.

Other conventional additives typically employed in shampoo compositions may be utilized. Fragrance oils, which mask the odor and provide cosmetic appeal, can be employed. Non-toxic and compatible dyes may be utilized to color the compositions, as desired. Preservatives, such as methyl paraben, propyl paraben and formaldehyde may be utilized.

In addition, other ingredients can be employed beneficially to provide shampoo compositions tailored to a specific use. For example, a sun screen additive such as octyl dimethyl para-aminobenzoic acid can be employed to provide hair protection. Also, products designed to provide dandruff protection can be formulated with agents such as zinc omadine (Olin).

The following examples, illustrating the novel ether sulfates of this invention, are presented without any intention that the invention be limited thereto.

EXAMPLE 1

Hexapropoxy-dodecaethoxy isodecyl sulfate, Na salt $$\text{iso-}C_{10}H_{21}(OC_3H_6)_6(OC_2H_4)_{12}OSO_3Na$$

(a) Preparation of hexapropoxy-dodecaethoxy isodecyl alcohol

To a reaction vessel are added, with stirring, 327 g of decyl alcohol (a mixture of primary, aliphatic alcohols, at least 90 mol % of which is branched 1-decanols, having a boiling range of 216° C. to 223° C., a specific gravity @ 20/20° C. of 0.838, a refractive index, $nD^{20}$, of 1.440, a pour point of $-65°$ F., a viscosity @ 20° C. of 22.5 centistokes and a solubility in water @ 20° C. of <0.05 g/100 g, and commercially available from Exxon Chemical Co.), 6.5 g of potassium hydroxide and 0.21 g of sodium borohydride. After heating the reaction mixture to 60° C. under 28 inches of vacuum (equivalent to 50 mm of mercury absolute pressure), the system is purged with nitrogen to atmospheric pressure and the evacuation and purging procedure is repeated two additional times to minimize the presence of air. Finally, a vacuum is pulled to 28 inches and the system is sealed then heated with agitation to 155° C. While maintaining the reaction temperature at 155° C., 720 g of propylene oxide are slowly added by use of a metering valve from a pressurized cylinder at such a rate that the pressure in the reaction vessel approaches and then is maintained at about atmospheric pressure. When the addition of propylene oxide is complete, the reaction mixture is allowed to post-react until the pressure drops to a point where it remains constant for at least 30 minutes. The system is cooled to 60° C. where the evacuation and purging procedure is repeated twice. Finally, a vacuum is pulled to 28 inches, and the system is sealed and heated to 155° C. where 1092 g of ethylene oxide are added by the procedure described above. After the post-react period, the system is cooled to 120° C. and a vacuum of 28 inches is applied for at least one hour to remove unreacted oxide. The system is cooled to 60° C., pressurized with nitrogen to atmospheric pressure and neutralized with about 6.3 g of acetic acid to yield a translucent pale yellow liquid of the formula

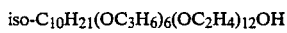

which becomes milky white upon cooling and develops a white precipitate upon standing.

Preparation of the title compound 258.8 g (0.25 moles) of the alcohol alkoxylate prepared in (a) above was added to a 3-neck reaction vessel and the system purged with nitrogen for 10 minutes. The reaction vessel was then evacuated and the alcohol alkoxylate therein was heated to 60° C. to remove any traces of water. After cooling to room temperature, 40 g (0.34 moles) of chlorosulfonic acid was added, with stirring, at a rate such that the reaction temperature remained between 30° and 35° C. throughout the addition. The reaction mixture was then stirred for an additional 90 minutes, after which time it was poured into ice and the pH adjusted to between 7.0 and 7.5 with a 50% solution of sodium hydroxide. Water was then added in an amount sufficient to adjust the solids level to between 40% and 45%.

EXAMPLE 2

Following essentially the procedure of Example 1(a) and employing the starting alcohol utilized in Example 1, i.e., the decyl alcohol available commercially from Exxon Chemical Co., and the appropriate amounts of propylene oxide and ethylene oxide, the following compounds are obtained:

(a) iso-$C_{10}H_{21}(OC_3H_6)_3(OC_2H_4)_9OH$
(b) iso-$C_{10}H_{21}(OC_3H_6)_3(OC_2H_4)_6OH$
(c) iso-$C_{10}H_{21}(OC_3H_6)_6(OC_2H_4)_6OH$; and
(d) iso-$C_{10}H_{21}(OC_3H_6)_9(OC_2H_4)_9OH$.

EXAMPLE 3

Following essentially the last step of the procedure in preparing the compound of Example 1, and using in place of the compound prepared in 1a), an approximately equivalent amount of compounds 2a)-2d), there was obtained:

(a) iso-$C_{10}H_{21}(OC_3H_6)_3(OC_2H_4)_9OSO_3Na$
(b) iso-$C_{10}H_{21}(OC_3H_6)_3(OC_2H_4)_6OSO_3Na$
(c) iso-$C_{10}H_{21}(OC_3H_6)_6(OC_2H_4)_6OSO_3Na$; and
(d) iso-$C_{10}H_{21}(OC_3H_6)_9(OC_2H_4)_9OSO_3Na$, respectively.

EXAMPLE 4

The foaming properties of the compounds of Examples 1 and 3a)-3d)were evaluated according to the Ross-Miles method described in Oil and Soap, Vol. 18, Pages 99–102 (1941). The Ross-Miles Foam Numbers indicated below are initial readings in millimeters of 0.1% solutions of the respective compounds in distilled water at a pH of 7.0 and at a temperature of 50° C.

| Compound | Ross-Miles Foam Number |
| --- | --- |
| Example 1 | 167 |
| Example 3a | 162 |
| Example 3b | 171 |
| Example 3c | 169 |
| Example 3d | 176 |

EXAMPLE 5

The eye irritation properties of the compounds of Examples 1 and 3a)-3d) were determined by the procedure suggested by Dr. Draize as described in "Appraisal of the Safety of Chemicals in Foods, Drugs and Cosmetics" published by the Association of Food and Drug Officials of the United States. Each of three normal healthy albino rabbits had 0.1 ml of an undiluted amount (~ 40–50% solids) of Examples 1, 3a), 3b), 3c) or 3d) instilled into the right eye, with no further subsequent treatment. The left eye of each animal was left untreated and was used as a control. Both eyes of each animal were examined every 24 hours for four days and then again on the seventh day. The scorings indicated below were made according to the Draize scale for scoring ocular lesions. The maximum possible score is 110 points, which indicates maximal irritation; zero score indicates no irritation.

| Compound | Draize Number |
| --- | --- |
| Example 1 | 0.0 |
| Example 3a | 2.0 |
| Example 3b | 23.3 |
| Example 3c | 25.0 |
| Example 3d | 10.3 |

EXAMPLE 6

The following represent typical formulations useful as shampoo compositions.

| | Percent | | |
| --- | --- | --- | --- |
| | A | B | C |
| Example 1 (41.7% act.) | 32.0 | 40.0 | — |
| Example 3a (40.7% act.) | — | — | 35.0 |
| lauramide diethanol amine | 6.0 | 2.0 | 5.0 |
| cocoamido hydroxypropyl sultaine (45% act.) | — | 6.0 | — |
| dye | 0.2 | 0.2 | 0.2 |
| perfume | 0.2 | 0.2 | 0.2 |
| water | q.s. | q.s. | q.s. |
| Total | 100.0 | 100.0 | 100.0 |
| pH (adjusted with citric acid or sodium hydroxide) | 6.0 | 6.0 | 7.0 |

What is claimed is:

1. A mild shampoo composition comprising, as the essential surfactant component, from about 5% to about 50% of a compound of formula I:

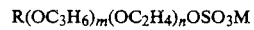
$$R(OC_3H_6)_m(OC_2H_4)_nOSO_3M \qquad I$$

wherein
R is the residue of a mixture of primary, aliphatic alcohols, at least 70 mol % of which is branched 1-decanols, the remaining components consisting essentially of primary, aliphatic alcohols having an average of 8 to 12 carbon atoms;
m is an integer 2 to 13;
n is an integer 6 to 15; and
M is a cation;
or a mixture of said compounds.

2. A composition according to claim 1 comprising, as the essential surfactant component, a compound of formula Ia:

$$R'(OC_3H_6)_{m'}(OC_2H_4)_{n'}OSO_3M' \qquad Ia$$

wherein
R' is the residue of a mixture of primary, aliphatic alcohols, at least 90 molt % of which is branched 1-decanols;
m' is an integer 3 to 12;
n' is an integer 6 to 13; and
M' is a cation selected from alkali metal, alkaline earth metal, ammonium, mono-, di- and tri-$C_2$-$C_4$ alkanolammonium and mono-, di-, tri- and tetra-$C_1$-$C_4$ alkylammonium;
or a mixture of said compounds.

3. A composition according to claim 2 comprising, as the essential surfactant component is compound of formula Ib:

$$R''(OC_3H_6)_{m''}(OC_2H_4)_{n''}OSO_3M'' \qquad Ib$$

wherein
- R'' is the residue of a mixture of primary, aliphatic alcohols, at least 95 mol % of which is branched 1-decanols;
- m'' is an integer 3 to 10;
- n'' is an integer 6 to 12; and
- M'' is an cation selected from sodium, potassium, ammonium, mono-, di- and tri-$C_2$–$C_4$-alkanolammonium and mono-, di-, tri- and tetra-$C_1$–$C_4$ alkylammonium;

or a mixture of said compounds.

4. A composition according to claim 3 comprising, as the essential surfactant component, a compound of formula Ic:

$$R'''(OC_3H_6)_{m'''}(OC_2H_4)_{n'''}OSO_3M''' \qquad \text{Ic}$$

wherein
- R''' is the residue of a mixture of primary, aliphatic alcohols, at least 95 mol % of which is branched 1-decanols and the major isomers are trimethyl-1-heptanols;
- m''' is an integer 3 to 9;
- n''' is an integer 8 to 12; and
- M''' is a cation selected from sodium, potassium, ammonium and mono-, di- and tri-$C_2$–$C_4$ alkanolammonium;

or a mixture of said compounds.

5. A composition according to claim 1 wherein the essential surfactant component is a mixture of compounds having the formula, $$\text{iso-}C_{10}H_{21}(OC_3H_6)_3(OC_2H_4)_6OSO_3Na$$

6. A composition according to claim 1 wherein the essential surfactant component is a mixture of compounds having the formula, $$\text{iso-}C_{10}H_{21}(OC_3H_6)_6(OC_2H_4)_6OSO_3Na$$

7. A composition according to claim 1 wherein the essential surfactant component is a mixture of compounds having the formula, $$\text{iso-}C_{10}H_{21}(OC_3H_6)_9(OC_2H_4)_9OSO_3Na$$

8. A composition according to claim 1 wherein the essential surfactant component is present in an amount of from about 5 % to about 40%.

9. A composition according to claim 8 wherein the essential surfactant component is present in an amount of from about 10% to about 30%.

10. A composition according to claim 1 wherein the essential surfactant component is a mixture of compounds having the formula, $$\text{iso-}C_{10}H_{21}(OC_3H_6)_6(OC_2H_4)_{12}OSO_3Na$$

11. A composition according to claim 1 wherein the essential surfactant component is a mixture of compounds having the formula, $$\text{iso-}C_{10}H_{21}(OC_3H_6)_3(OC_2H_4)_9OSO_3Na.$$

* * * * *